United States Patent [19]
Arnsten et al.

[11] Patent Number: 5,863,934
[45] Date of Patent: Jan. 26, 1999

[54] USE OF LOFEXIDINE IN THE TREATMENT OF BEHAVIORAL DISORDERS

[75] Inventors: Amy F. T. Arnsten, 376 Sperry Rd., Bethany, Conn. 06524; Patricia S. Goldman-Rakic, 253 St. Ronan Dr., New Haven, Conn. 06511; Robert D. Hunt, Nashville, Tenn.

[73] Assignees: Amy F. T. Arnsten, Bethany; Patricia S. Goldman-Rakic, New Haven, both of Conn.; Robert H. Hunt, Nashville, Tenn.

[21] Appl. No.: 734,464

[22] Filed: Oct. 17, 1996

Related U.S. Application Data

[63] Continuation-in-part of Ser. No. 531,643, Sep. 21, 1995.
[51] Int. Cl.$^6$ .................................................. A61K 31/415
[52] U.S. Cl. ................................................ 514/401
[58] Field of Search ..................................... 514/617, 634, 514/401

[56] References Cited

U.S. PATENT DOCUMENTS 4,404,226  9/1983  Matejcek et al. .

OTHER PUBLICATIONS

Hunt et al, J. Amer. Acad. Child Psych., vol. 24, pp. 617–629, 1985.

Chappell et al, Derwent Drug File Abstracts, abstract No. 95–27904, 1994

Kunchandy et al, Chemical Abstracts, vol. 105, No. 23, abstract No. 203125d, 1986.

*Primary Examiner*—William R. A. Jarvis
*Attorney, Agent, or Firm*—Clark & Elbing LLP

[57] ABSTRACT

Disclosed is a method of treating disorders which have prominent symptoms of behavioral disinhibition (e.g., Attention-Deficit Hyperactivity Disorder, Conduct Disorder, Oppositional Defiant Disorder, Tourette's Syndrome, Lesch-Nyhan Syndrome, or the disinhibitory symptoms accompanying Post-traumatic Stress Disorder or dementia) in a primate with minimal sedative side effects by administering thereto a therapeutically effective amount of lofexidine.

10 Claims, 9 Drawing Sheets

USE OF LOFEXIDINE IN THE TREATMENT OF BEHAVIORAL DISORDERS

CROSS-REFERENCE TO RELATED APPLICATIONS

This application is a continuation-in-part of application Ser. No. 08/531,643, filed Sep. 21, 1995.

STATEMENT AS TO FEDERALLY SPONSORED RESEARCH

This invention was made with United States government support under contracts RO1 MH44866 from the National Institute of Health and Contract RO1 AG06036 from the National Institute of Aging.

BACKGROUND OF THE INVENTION

Attention-Deficit/Hyperactivity is a major disorder of childhood which often continues into the adult years. Patients with Attention-Deficit/Hyperactivity have difficulty concentrating and organizing their behavior. In addition, they are impulsive and easily distracted. Some display major hyperactivity while others outgrow or never show the motor symptoms. Attention-Deficit/Hyperactivity affects about 3.5 million children and adolescents in the United States, about half of whom retain attentional difficulties into adulthood (Cantwell and Baker, 1988). Attention-Deficit/Hyperactivity can result in low self-esteem, poor relationships with peers and adults, and inferior performance in school. These difficulties can lead to serious emotional problems, truancy, drug abuse and criminal behavior (Pelham and Murphy, 1986). Moreover, the symptoms of Attention-Deficit/Hyperactivity commonly accompany those of Conduct Disorder (inappropriate aggression) and Tourette's Syndrome (inappropriate movements). Many of these same symptoms of disinhibited, inappropriate behaviors are also observed in elderly, demented individuals (e.g., agitation, wandering, inappropriate aggression). These disinhibited behaviors pose a serious problem to nursing homes and other caregivers.

This spectrum of disinhibited behaviors may arise from a dysfunction of the prefrontal cortex (Arnsten, A. F. T., Steere, J. C., Hunt R. D., (1996). The contribution of alpha-2 noradrenergic mechanisms to prefrontal cortical cognitive function: Potential significance to Attention Deficit Hyperactivity Disorder. Arch. Gen. Psychiatry 53:448–455.). The prefrontal cortex projects to the brain's motor areas (striatum, motor cortices; Goldman-Rakic, P. S. et al., (1992) The Prefrontal Cortex and Internally Generated Motor Acts, Current Opinion Neurobiol. 2:830–835) and thus functions to guide behavior appropriately. In addition, the prefrontal cortex may perform this function for intellectual and affective behaviors. Degeneration of the prefrontal cortex may produce disinhibited behavior in elderly demented individuals, while altered development of these systems may lead to childhood disorders such as Attention-Deficit/Hyperactivity, Conduct Disorder, and Tourette's Syndrome.

The ventromedial/orbital PFC (vm/orbPFC) is thought to play an essential role in behavioral calming, and thus drugs which improve vm/orbPFC function may represent an important advance in pharmacological treatment for behavioral disorders. In particular, treatments that improve vm/orbPFC function may be able to calm behavior without inducing sedation. In contrast to the dorsolateral PFC (dlPFC) which is important for attention regulation, the vm/orbPFC is thought to be more involved in regulation of emotional behavior and suppression of inappropriate behaviors. Lesions of vmPFC and/or orbital PFC in humans can produce immature behavior, lack of restraint, and increased motor activity (e.g. Blumer & Benson, 1975); Luria, 1966; Miller, 1992; Stuss et al., 1992). In monkeys, lesions localized to the ventral surface of the PFC have also been shown to produce locomotor hyperactivity (Ruch & Shenkin, 1943), hyper-reactivity to environmental stimulation, and altered aggression (Butter et al., 1970). These cortical areas have strong reciprocal connections with the amygdala (e.g. Morecraft et al., 1992), providing an opportunity to regulate the expression of aggressive and emotional behavior. Lesions of the vm/orbPFC impair reversal of object or spatial discrimination problems without altering original acquisition performance (Dias et al., 1996; Iversen & Mishkin, 1970; McEnancy & Butter, 1969; Mishkin et al., 1969; Oscar-Berman, 1978; Ridley et al., 1993). Impaired reversal performance is especially persistent following orbital PFC lesions (Butter, 1969; Iversen & Mishkin, 1970). Importantly, monkeys with orbital lesions are also disproportionately impaired in suppressing a response to a preferred stimulus independent of baiting conditions produced by the experimenter (Mishkin, 1964). Aged monkeys are also impaired on reversal, but not acquisition of discrimination problems, consistent with orbital PFC dysfunction with age (Bartus et al., 1979; Rapp, 1990).

Because recent research efforts have focused almost exclusively on developing treatments for the memory problems of dementia, there have been few new treatments for this spectrum of disorders. This focus has resulted in little research directed to the disorders of childhood. Attention-Deficit/Hyperactivity is usually treated with methylphenidate (Ritalin™ commercially available from Ciba Pharmaceutical), an amphetamine-like compound which is helpful for many patients (Hunt et al., 1991). However, methylphenidate has many deleterious side-effects including insomnia, appetite suppression, irritability, attentional "sticking", perseverative thoughts, increased aggression, and stunted growth (Hunt, R. D. (1988) Attention Deficit Disorder: Diagnosis, Assessment and Treatment. In Handbook of Clinical Assessment of Children and Adolescents—A Biopsychosocial Approach. C. Kestenbaum and D. Williams (eds.), pp. 519–561; McBurnett et al., 1991; Tannock and Schachar, 1992). Moreover, methylphenidate is contraindicated in patients with Conduct Disorder or Tourette's Syndrome because it can aggravate aggression and tics. Because many patients cannot tolerate methylphenidate, or find it only partially effective, alternative medications would be beneficial.

One alternative treatment for behavioral disorders has been the alpha-2 adrenergic agonist, clonidine (Hunt, R. D. et al., (1985) Clonidine Benefits Children with Attention Deficit Disorder and Hyperactivity: Report of a Double-Blind Placebo-Controlled Crossover Study, J. Amer. Acad. Child Psych., 24(5):617–629; 1986). Clonidine is particularly useful in Attention-Deficit/Hyperactivity patients who are very aggressive and/or highly aroused (Hunt, R. D. et al., (1990) Clonidine in Child and Adolescent Psychiatry, J. Child & Adol. Psychopharm., 1:87–101). However, it also has significant adverse side effects, including hypotension, "withdrawal" effects due to its short half life, and excessive sedation (ibid). It has been commonly assumed that the sedative action of clonidine is responsible for its beneficial effects in Attention-Deficit/Hyperactivity patients. It was presumed that clonidine attenuates noradrenergic tone, thereby decreasing arousal to near optimal levels (ibid). It was also presumed that clonidine improved Tourette's syndrome by a similar mechanism (Leckman, J. F. et al., (1989)

Clonidine Treatment of Gilles de la Tourette Syndrome, Arch. Gen. Psychiatry, 48 324–328). Thus, even though the sedation itself often interfered with academic performance and other activities, the sedative side effects of clonidine treatment were thought to be essential for the beneficial effects of the drug.

Guanfacine, another alpha -2 adrenergic agonist, is less sedating than clonidine in monkeys (Arnsten, A. F. T. et al. (1988) The alpha-2 adrenergic agonist guanfacine improves memory in aged monkeys without sedative or hypotensive side effects: Evidence for alpha-2 receptor subtypes, J. Neurosci., 8: 4287–4298) and in humans (Kugler, J. et al., (1980) Differences in Psychic Performance with Guanfacine and Clonidine in Normotensive Subjects, Br. J. Clin. Pharmacol. 99:803–809). However, because clonidine was presumed to have its beneficial effects through its sedating actions, guanfacine was assumed to be less effective than clonidine in treating Attention-Deficit/Hyperactivity and related disorders. Very low doses of guanfacine (e.g. 0.00001–0.001 mg/kg) or moderate does of clonidine (about 0.01–0.05 mg/kg) improve working memory performance in aged monkeys without hypotensive or sedative side effects (Arnsten, A. F. T. et al., U.S. Pat. No. 4,847,300 which is incorporated herein by reference; Arnsten, A. F. T. et al., (1985) Alpha-2 adrenergic mechanisms in prefrontal cortex associated with cognitive decline in aged non-human primates, Science, 230:1273–1276; Arnsten, A. F. T. et al., (1988) The alpha-2 adrenergic agonist guanfacine improves memory in aged monkeys without sedative or hypotensive side effects: Evidence for alpha-2 receptor subtypes, J. Neurosci., 8:4287–4298). In addition, very low doses (0.000011–0.0011 mg/kg) of guanfacine enhanced working memory and attention regulation in aged monkeys (Arnsten, A. F. T. et al., (1992) Alpha-2 adrenergic agonists decrease distractibility in aged monkeys performing a delayed response task, Psychopharm. 108:159–169). The beneficial effects of guanfacine were particularly evident under conditions where distracting stimuli were present (ibid).

Lofexidine (2-{α-(2,6-dichlorphenoxy)-ethyl}-AE$^2$-imidazoline) is an investigational α-2-adrenergic agonist which is an antihypertensive similar to clonidine. Animal studies have shown that lofexidine lowers blood pressure (Burke J T, Koch-Weser J (1977) Lofexidine, a new centrally acting antihypertensive. Clin Pharmacol Ther 21: 99–100; Timmerman PBNWN, van Zweitan PA (1981). Correlations between central and hypotension and peripheral hypertensive effects of structuraly dissimilar alpha-adrenoreceptor agonists. Life Sci 28: 653–660; Graf E, Doppelfeld I S, Prop G (1982) Animal experiments on the cardiovascular effects of lofexidine. Arzneimittel-Forschung 32: 941–955), and some animal studies have shown that lofexidine may be less sedating than clonidine (Graf E, Sieck A, Wenzl H and Winkelmann J (1982) Animal experiments on the safety pharmacology of lofexidine. Arzneimittel-Forschung 32: 931–940). Clinical studies (Lopez, L M and Mehta J L (1984) AM. J. Cardiol 53: 787–790) have shown that lofexidine is significantly less potent than clonidine in decreasing blood pressure in hypertensive patients (lofexidine mean dose of 0.83 mg±0.54 mg twice daily; clonidine mean dose 0.48±0.29 mg twice daily). Lofexidine also produced fewer side effects than clonidine. In particular, clonidine produced significantly more dizziness and drowsiness than lofexidine (ibid; and Wilkins L H, Winternitz S R, Oparil S, Smith L R and Dustan H P (1981) Lofexidine and clonidine in moderate essential hypertension. Clin. Pharmacol. Ther. 30: 752–807). Lofexidine is also under investigational use for the treatment of opiate withdrawal (reviewed in Cox S and Alcorn R (1995) Lofexidine and opioid withdrawal. Lancet 345: 1385–1386). These studies indicate that lofexidine can decrease withdrawal signs with fewer sedative and hypotensive side effects than clonidine (Washton A M, Resnick R B, Geyer G (1983) Opiate withdrawal using lofexidine, a clonidine analogue with fewer side effects. J Clin Psychiatry 44: 335–337).

Because of the large patient population suffering from behavioral disinhibition and the deficiencies associated with existing therapies, a significant need exists for a method of treating behavioral disinhibition having a low incidence of adverse side-effects, especially sedation.

SUMMARY OF THE INVENTION

The present invention features the use of an alpha-2A agonist for the treatment of behavioral disinhibition. More particularly, the present invention relates to the improvement of behavioral inhibition in patients with Attention-Deficit Hyperactivity Disorder, Conduct Disorder, Oppositional Defiant Disorder, Tourette's Syndrome, Lesch-Nyhan Syndrome, or the disinhibitory symptoms accompanying Post-traumatic Stress Disorder or dementia following treatment with either of the alpha-2A agonists, guanfacine and lofexidine. The symptoms improved by guanfacine and lofexidine treatment include, but are not limited to: agitation, hyperactivity, distractibility, inattention, impulsivity, disorganization, uncontrolled aggression, self-mutilation, and uncontrolled movements.

The method of the invention provides a method for treating a behavioral disinhibition in a primate without inducing excessive sedation. Preferably, the method is used for the treatment of hyperactivity, agitation, impulsivity, aggression, inattention, distractibility, disorganization, uncontrolled movements, and self-mutilation. Other alpha-2A agonists useful in the invention are UK14304, and guanabenz. Most preferably, the alpha-2A agonist is guanfacine or lofexidine.

The current studies examined the effects of the alpha-2A agonists guanfacine and lofexidine on the performance of cognitive tasks reliant on the prefrontal cortex, a brain region essential for behavioral regulation and inhibition of inappropriate responses. Guanfacine and lofexidine were examined for effects on the delayed response task, a test of spatial working memory tightly linked to the integrity of the dorsolateral prefrontal cortex, in young and aged monkeys. Animals were also rated for changes in behavior (e.g. sedation), and the overall drug profiles were compared to the nonspecific alpha-2 agonist, clonidine. In addition, the current study also explored the hypothesis that higher guanfacine doses might calm behavior through enhancement of vm/orbPFC function, by characterizing guanfacine's effects on performance of an object discrimination reversal task. Aged monkeys were treated with low vs. high doses of guanfacine and tested on reversal conditions of a visual object discrimination problem. We found that high (0.1–0.5 mg/kg) but not low (0.00001–0.001 mg/kg) doses of guanfacine improved reversal performance, indicating that higher guanfacine doses may improve vm/orbPFC inhibitory functions. Importantly, the 0.1 mg/kg guanfacine dose was able to improve reversal performance without any evidence of sedation, again demonstrating that the calming effects of alpha-2 agonists can be dissociated from their sedating properties.

In another aspect of the invention, alpha-2A agonists, in particular guanfacine and lofexidine, can also be used, at the dosages described above, for the treatment of the prefrontal cortical cognitive dysfunction that accompanies schizophrenia. These prefrontal symptoms are generally unresponsive to neuroleptic therapy.

Other features and advantages of the invention will be apparent from the following description of the preferred embodiments thereof, and from the claims.

DESCRIPTION OF THE PREFERRED EMBODIMENTS

The present invention is based on our discovery that the administration of guanfacine or lofexidine calms behavior without concomitant sedation in juvenile, adult or elderly primates with symptoms of behavioral disinhibition including hyperactivity, agitation, impulsivity, aggression, inattention, distractibility, disorganization, uncontrolled movements, and/or self-mutilation.

Figure 1:
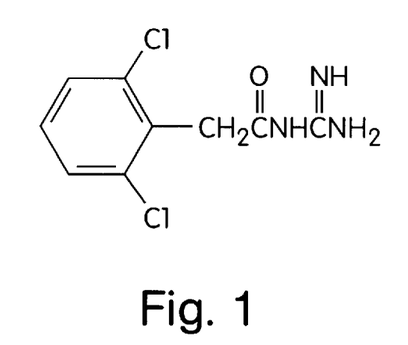
FIG. 1 is the chemical structure of guanfacine.

Referring to FIG. 1, the preferred active compound of the present invention is guanfacine (N-(Aminoiminomethyl)-2,6-dichlorobenzeneacetamide; N-amidino-2-(2,6 dichlorophenyl) acetamide). Guanfacine (Tenex™, commercially available from Wyeth Ayerst) is an alpha-2 noradrenergic agonist which has been available as an FDA approved hypotensive agent for over two decades. Guanfacine has several significant advantages compared to clonidine. Guanfacine has a longer excretion half-life (18 hours in adults; Sorken, E. M. et al., (1986) Guanfacine: A review of its pharmacodynamic and pharmacokinetic properties, and therapeutic efficacy in the treatment of hypertension, Drugs 31:301–336), and is less sedating and less hypotensive than clonidine (Kugler, J. et al., (1980) Differences in psychic performance with guanfacine and clonidine in normotensive subjects, Br. J. Clin. Pharmacol. 99:803–809). Guanfacine also has a more selective receptor binding profile than clonidine. Unlike clonidine, guanfacine does not bind significantly to alpha-1 receptors (Sorkin, E. M. et al., (1986) Guanfacine: A review of its pharmacodynamic and pharmacokinetic properties, and therapeutic efficacy in the treatment of hypertension, Drugs 31:301–336) or imidazoline receptors (Vigne, P. et al., (1989) Guanabenz, guanachlor, guanoxan, and idazoxan bind with high affinity to non-adrenergic sites in pig kidney membranes, Eur. J. Pharmacol., 160:295–298; Brown, C. M. et al., (1990) Alpha-2-adrenoceptor subtypes and imidazoline-like binding sites in the rat brain, Br. J. Pharmacol., 99:803–809). Guanfacine also displays a more selective profile within the family of alpha-2 receptors. Whereas clonidine binds equally well at the alpha-2A, alpha-2B, and alpha-2C subtypes, guanfacine exhibits selective binding for the alpha-2A site (Uhlen, S. et al., (1991) Delineation of rat kidney alpha 2A- and alpha 2B-adrenoceptors with [$^3$H] RX821002 radioligand binding: computer modelling reveals that guanfacine is an alpha 2A-selective compound, Eur. J. Pharmacol., 202:235–243).

We found that a low dose of guanfacine (0.001 mg/kg) was ineffective in a hyperactive, inattentive young monkey (see Table 1), but that higher doses of guanfacine do enhance prefrontal function and calm behavior without producing sedation. More particularly, higher doses of guanfacine improve behavior in hyperactive, inattentive, and impulsive young monkeys without the concomitant sedation associated with clonidine treatment. Guanfacine treatment similarly benefits human subjects with symptoms of behavioral disinhibition. Other compounds related to guanfacine that might be effective in the methods of the invention include all agonists with relative selectivity for the alpha-2A subtype of adrenergic receptor, such as UK14304 and guanabenz, or lofexidine.

EXAMPLES

General

The examples described herein report an evaluation of the effects of an alpha-2A adrengeric agonist, guanfacine, on cognitive performance and behavioral ratings in monkeys and on behavioral ratings in human patients.

Subjects

The first group of animals used in the following examples were six peri-adolescent young rhesus monkeys (*Macaca mulatta*) (approximate ages of 2–5 years), 1 male and 5 female, and 4 female aged monkeys (approximate ages of 20–35 years). The monkeys were housed and cared for at Yale University School of Medicine, New Haven, Conn. The second group of animals used in this study were 6 female rhesus monkeys ranging in age from about 20 to over 35 years of age.

The human subjects consisted of children and adolescents with a range of behavioral disorders referred to one of the inventors, Dr. Hunt, for treatment at the Center for Attention and Related Disorders, Nashville, Tenn.

Subjects having Attention-Deficit/Hyperactivity Disorder included thirteen children and adolescents ranging in age from 4–20 (mean 11.1 years) (11 male and 2 female) with a DSM-IV diagnosis of Attention-Deficit/Hyperactivity Disorder. In addition, three subjects met criteria for Oppositional Defiant Disorder and one for learning disabilities. This group constitutes a population of middle class, motivated and cooperative subjects. Informed consent was obtained verbally and in writing after reviewing the potential benefits, side effects, and investigational nature of the use of guanfacine.

Guanfacine was also tested in six children and adolescents, ranging in age from 5 to 15 years, who met DSM-IV criteria for Tourette's syndrome.

Cognitive Testing (Monkey Studies)

In the following examples, the cognitive function of the prefrontal cortex was assessed using the Delayed Response Task Test (especially sensitive to changes in dorsolateral prefrontal cortex function, P. S. Goldman-Rakic, 1987) and the Visual Object Reversal task (especially sensitive to changes in ventromedial or orbital prefrontal cortical function; Butter, 1969; Iversen & Mishkin, 1970). Animals tested for highly palatable food rewards to optimize motivation. The experimenter testing the animal ws unaware of the drug treatment conditions. All drug responses were compared to matched saline control responses. Relevant measures consisted of number of completed and correct trials. In the delayed response task, five different delay lengths were used in the 30 trials which comprises a daily test session; animals were tested twice a week with 3–4 days separating test sessions. In the visual object discrimination task, the animals were tested daily for 40 trials/session. In the first day of each week, the animal was presented with a new discrimination problem. The animal was presented with 3 new objects, only one of which was associated with food reward. Following two consecutive days of criterion level performance ($\geq 36/40$ trails correct), the reward contingencies were reversed, and a previously unrewarded object became the reinforced stimulus. This condition was termed "reversal performance". Importantly, the object chosen for reinforcement on the reversal condition was the object least preferred by the animal; i.e., the previously non-rewarded object that was selected the least number of times when the monkey made errors.

Rating Scales (Monkey Studies)

Two rating scales were utilized by the experimenter testing the monkey. One rating sale assessed the levels of sedation and the other assessed levels of aggression/docility. The ratings of sedation were as follows: 0=normal level of arousal; I=quiet or calm; II=sedated (drooping eyelids, slowed movements); III=intermittent sleeping; and IV=too sedated to finish testing. The ratings of agitation were as follows: -I=very alert; -II=slight agitation; -III=pronounced agitation; and -IV=too agitated to complete testing. Detailed descriptions of unusual behavior or behavioral changes were noted, including changes in aggressive or self-mutilatory behaviors.

Rating Scales (Clinical Studies)

Attention-Deficit/Hyperactivity symptoms were assessed using the Conners rating scales (Conners, C. K., (1973) Rating scales for use in drug studies with children, Amer. J. of Psych., 126:884–888) and related measures (Milich, R. et al., (1982) The independent dimensions of hyperactivity and aggression: A validation with playroom observation data, J. Abnormal Psych., 91:183–198). Follow-up measures using the same ratings were administered approximately one month after the initiation of guanfacine treatment.

Motor and phonic tics were assessed in patients with Tourette's Syndrome using a parent rated, 4 point tic rating scale as follows: 0 (no tics observed); 1 (mild tics observed; approximately less than one per hour); 2 (moderate tics observed; approximately one per five minutes); 3 (severe tics observed; approximately one or more per minute).

Drug Administration

Monkeys were injected intramuscularly with an acute dose of guanfacine (0.00001–0.86 mg/kg), clonidine (0.02–0.05 mg/kg) or saline, 2 hours (guanfacine) or 15 min. (clonidine) prior to cognitive testing/behavioral assessment. There was generally at least a one week washout period between drug doses. Guanfacine and clonidine were dissolved in sterile saline under aseptic conditions.

Human subjects received chronic, oral guanfacine (Tenex™, 1 mg tablets) treatment.

Pharmacologic Treatment

In order to minimize side effects in patients, guanfacine dosages were gradually increased from a low initial dosage of 0.5 mg/day to as much as 4 mg/day with a 0.5 mg increment every third day. Dosages were individually titrated for optimal clinical response. When patients were changing from other medications, the dosage of guanfacine was gradually increased while the previous medications were gradually decreased. The mean therapeutic dosage was 3.2 mg/day (0.091 mg/kg/day). Therapeutic administration at peak dose was generally divided into 0.5 mg in the morning, 0.5 mg at noon, 0.5 mg at approximately 4 pm, and 1.0 mg before bedtime. Thus, doses were about 0.01 mg/kg during the day and about 0.03 mg/kg at bedtime.

Design and Analysis

Monkey data were analyzed using, within subjects, comparisons of performance on drug versus matched saline control. Delayed response performance was assessed using a paired t-test (t dep), visual object discrimination reversal performance was assessed using an analysis of variance with repeated measures with post-hoc tests, while rating scale data utilized nonparametric statistics (Wilcoxon test). The p value for analyzing the monkey data was always $p<0.05$ for achieving significance.

To maintain the closest possible correlation with actual clinical practice, the initial investigation was conducted using a within subjects design. Dependent measures consisted of Conners' Attention-Deficit/Hyperactivity Disorder factor scores as well as changes in specific items on the Conners' Parent Questionnaire. Specific item differences were measured in anticipation of patterns of change resulting from guanfacine treatment that would not be identified by the specific item clusters defined by factor analysis. Therefore, the most specific patterns of change induced by this new treatment could be delineated. Statistical analysis utilized paired t-tests.

Example 1
THE EFFECT OF ADMINISTERING CLONIDINE TO A YOUNG MONKEY

In Examples 1 and 2, drugs were administered to young monkeys with marked symptoms of hyperactivity, distractibility, inattention and aggressive behaviors due to longstanding personality traits or to the stress of recent entry into the colony. In addition, some of these animals exhibited self-mutilatory behaviors (e.g., self-biting). These symptoms disrupted normal cognitive testing. Example 1 involved prior art treatment with clonidine, while Example 2 employed guanfacine treatment of the invention.

Clonidine (0.02–0.05 mg/kg) or saline was administered to one young male (#636) and one young female (#643) rhesus monkey. Following saline administration, the monkeys were too agitated to test, completing an average of only 6 and 10 of the 30 trials attempted, respectively. Accuracy of response was also poor, averaging only 53.5% correct. Following 0.04 mg/kg clonidine, monkey #643 was too sedated to test. In contrast, 0.02 mg/kg clonidine improved performance markedly. This dose of clonidine was administered to this monkey on six separate occasions and each time the monkey completed all 30 trials. Accuracy of performance also improved to an average of 77% correct. Following saline administration, monkey #643 completed 10 of the 30 trials attempted, with only 40.0% chosen correctly. In contrast, following clonidine treatment (0.05 mg/kg), the monkey completed all 30 trials, performing 77% correct.

Figure 2A:
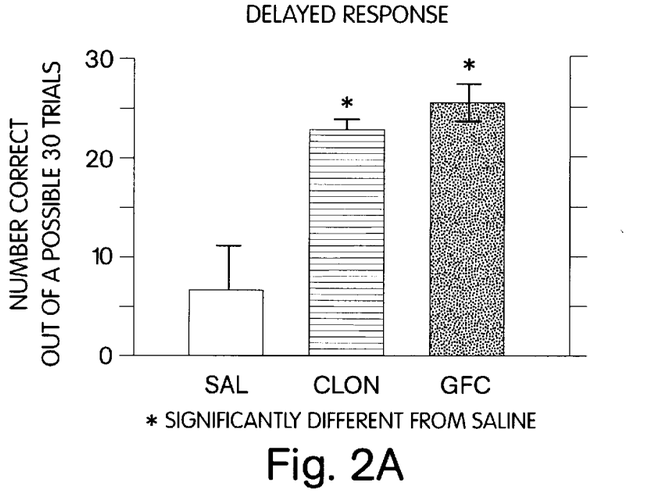
FIGS. 2A and 2B are histograms depicting the effect of guanfacine treatment in young, agitated monkeys.
Figure 2B:
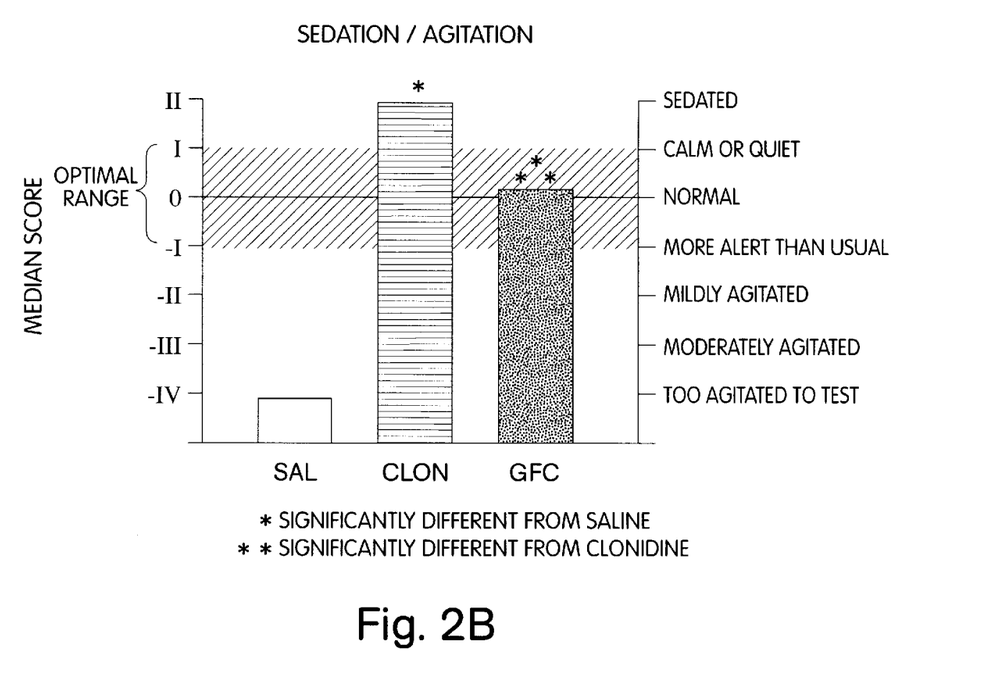
Figure 3A:
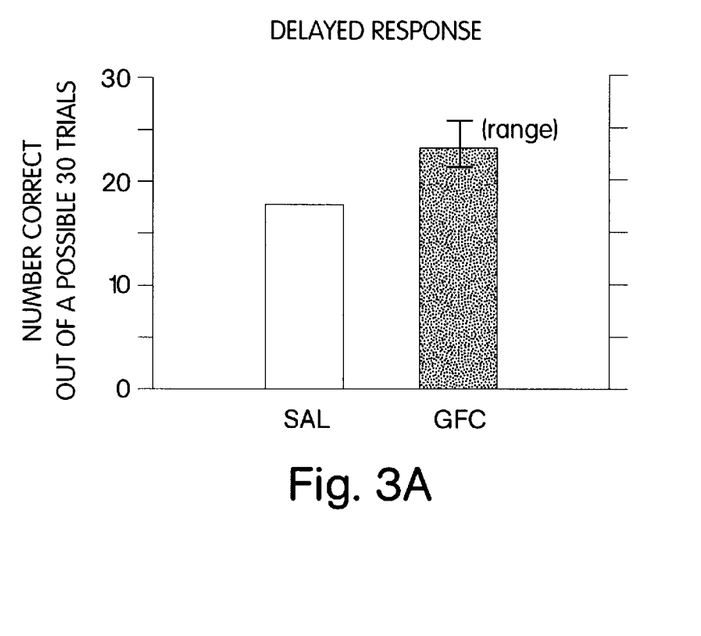
FIGS. 3A and 3B are histograms depicting the effects of guanfacine in aged, agitated monkeys.
Figure 3B:
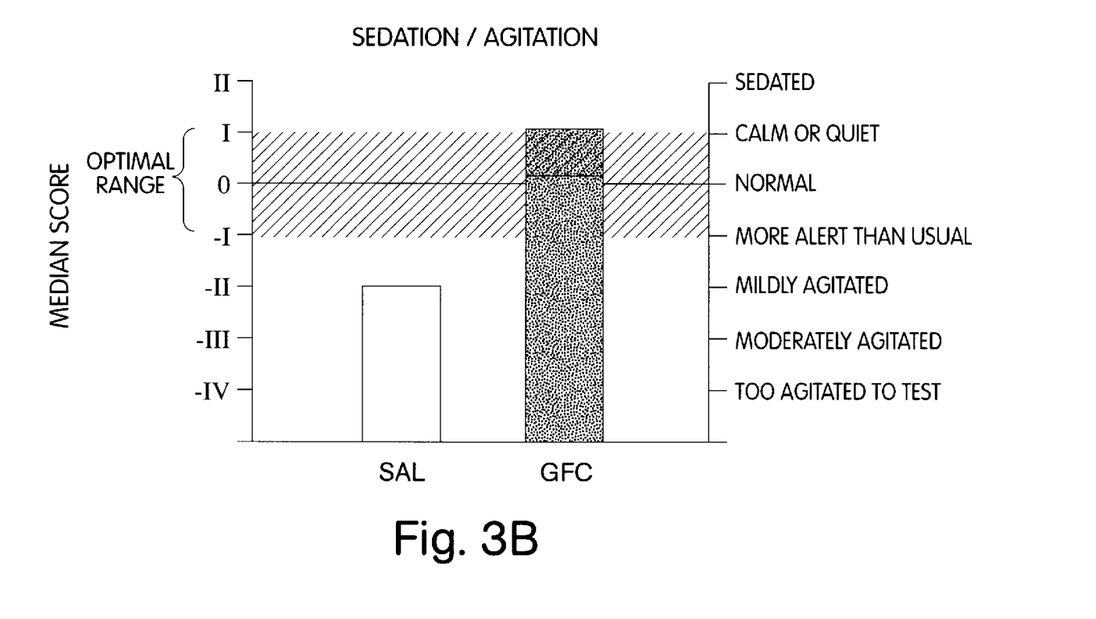

Marked sedation accompanied the improved performance of both animals. The median sedation score for both monkeys was a rating of II (i.e., sedated, drooping eyelids, slowed movements). A summary of these data can be seen in FIG. 2. This experimental profile is similar to the clinical effects of clonidine, where beneficial effects of clonidine are accompanied by significant sedation. This pattern of results suggested that the calming effects of clonidine result from its sedating actions.

Example 2
THE EFFECT OF ADMINISTERING GUANFACINE TO YOUNG MONKEYS

Guanfacine was administered to the two young monkeys who had previously received clonidine. Although the lowest dose of guanfacine (0.001 mg/kg) did not improve the behavior of monkey #636, behavior became progressively better with increasing dose (see Table 1). Maximal improvement occurred with guanfacine doses ranging between 0.11–0.53 mg/kg range. Monkey #643 was tested repeatedly with 0.53 mg/kg guanfacine and was consistently improved (see Table 2). Importantly, neither animal exhibited symptoms of sedation following calming doses of guanfacine. A summary of the clonidine and guanfacine data can be seen in FIG. 2.

The calming effects of guanfacine were assessed in four additional adolescent female monkeys. The results of the monkey experiments are expressed as mean +/−S.E.M. These four monkeys completed an average of $11.1\pm2.1$ of the 30 trials attempted and performed an average of $6.4\pm1.3$ trials correctly following saline treatment. In contrast, the monkeys completed an average of $29.3\pm0.9$ trials and performed an average of $23.1\pm1.8$ correctly following 0.5 mg/kg guanfacine. Guanfacine also decreased agitation ratings without inducing sedation. Median agitation scores were $-3.1\pm0.4$ (i.e., agitation interfering with testing) and $-0.4\pm0.7$ (i.e., normal to more alert) following saline and guanfacine, respectively.

When the results from the six monkeys were combined for statistical analysis, guanfacine (0.5 mg/kg) improved significantly the number of trials completed (saline: $9.4\pm1.7$; guanfacine: $29.5\pm0.6$; t dep=9.41, df=5, p=0.0002) and the number of trials correct (saline: $5.6\pm0.9$; guanfacine: $22.7\pm1.4$; t dep=9.63, df=5, p=0.0002). This same dose of guanfacine significantly reduced agitation ratings without inducing sedation (saline: median score of $-3.4\pm0.3$; guanfacine: median score of $-1.1\pm0.5$; Wilcoxon p=−0.028). Guanfacine was also significantly less sedating than clonidine (Wilcoxon test on clonidine vs. guanfacine: p=0.004). Thus, guanfacine significantly calmed behavior without inducing sedation.

The experimenter's observations of the animals indicated that the monkeys exhibited fewer disinhibited behaviors following guanfacine treatment (see e.g. Tables 1 and 2). The monkeys engaged in less hyperactivity, circling, vocalization, aggression directed at the experimenter, self-mutilation (i.e., specifically a decrease in self-biting), and less inattentive or distracted behaviors. The animals appeared more focused, calm, and in control of their behavior.

Example 3
THE EFFECT OF ADMINISTERING GUANFACINE VS. CLONIDINE TO AGED MONKEYS

The effects of administering guanfacine to aged monkeys with symptoms of behavioral disinhibition can be seen in Table 3. These highly-trained aged animals consistently completed all 30 trials of a test session. However, mild agitation interfered with accuracy of response in two monkeys (#447 and #124). Monkey #447 also exhibited aggressive behaviors following incorrect responses. Two additional animals (#446 and #448) who did not display agitation, but were very aggressive, provided the opportunity to observe the effects of guanfacine effects on aggression.

Similar to the effects in young monkeys, guanfacine (0.011–0.53 mg/kg) produced calming effects in aged monkeys. Agitation in monkeys #447 and #124 and aggression in monkeys #446, #447 and #448 were improved. These beneficial effects were observed without inducing sedation.

In contrast to guanfacine, the beneficial effects of clonidine were accompanied by sedative effects. Examples of the effects of clonidine can be seen in Table 4. Although these data were collected prior to the development of the agitation/sedation rating scales currently used, the experimenters' comments indicate that clonidine produced marked sedation.

Figure 9A:
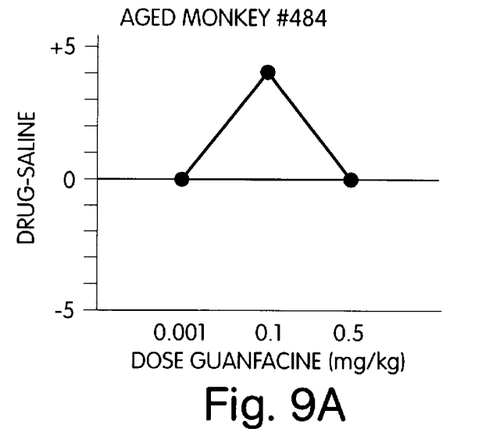
FIGS. 9A, 9B, and 9C are graphs illustrating the relationship between higher guanfacine doses and vm/orbPFC-related tasks in aged monkeys.

Example 4
THE EFFECTS OF GUANFACINE ON REVERSAL OF VISUAL OBJECT DISCRIMINATION PERFORMANCE IN AGED MONKEYS Low (0.00001–0.001 mg/kg) vs. higher (0.1 and 0.5 mg/kg) doses of guanfacine were administered to aged monkeys performing a visual object discrimination reversal task that relies on the inhibitory functions of the ventromedial/orbital PFC. Guanfacine treatment produced a dose-related improvement in reversal performance (FIG. 9, parts A (individual dose/response curve) and C (mean response of 6 aged monkeys)). A one-way analysis of variance with repeated measures showed a significant effect of drug (F(3,15)=9.21, p=0.001). Post-hoc tests showed that reversal performance was improved compared to vehicle following the 0.1 mg/kg (F(1,5)=31.97, p=0.002) and 0.5 mg/kg ((F(1,5)=19.55, p=0.007) doses, but was not significantly improved by low dose (0.00001–0.001 mg/kg) guanfacine treatment (F(1,5)=0.003, p=0.96; FIG. 9, part C). These data suggest that low doses of guanfacine may be affecting dlPFC, but not vm/orbPFC function, while higher doses may produce more global PFC improvement needed for behavioral calming. This interpretation is supported by the finding that these low doses of guanfacine similarly were not able to calm behavior in agitated, disinhibited young monkeys (see Table 1).

Figure 9B:
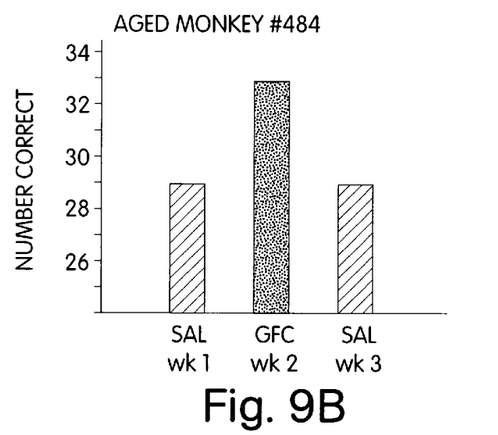
Figure 9C:
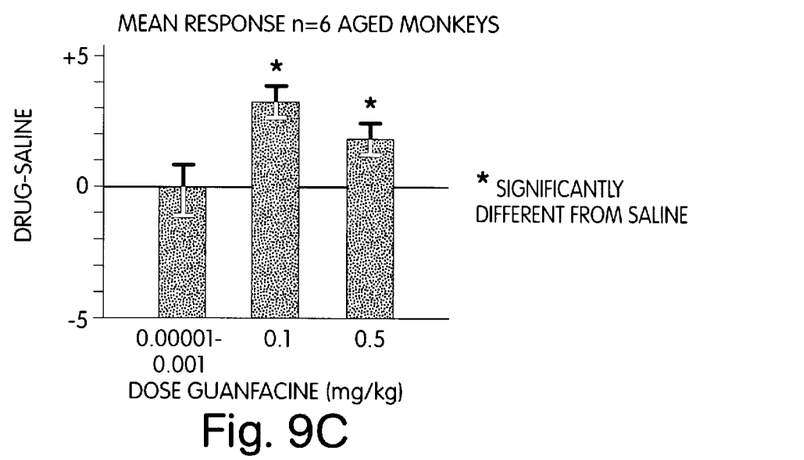

The improvement following the higher guanfacine doses was not simply due to practice effects, as performance decreased toward baseline levels the following week with vehicle administration (e.g. FIG. 9, part B). The 0.1 mg/kg guanfacine response was analyzed further to better elucidate the nature of the drug effect. On the reversal day, two types of errors were possible: 1) choice of the previously rewarded stimulus (i.e., the correct stimulus during acquisition performance), or 2) choice of the never-rewarded stimulus. It is important to note that the never-rewarded stimulus was the object most preferred by the animal during acquisition trials. Guanfacine had no significant effect on choice of the previously rewarded stimulus (mean ±S.E.M. errors vehicle: $9.0\pm1.5$; mean ±S.E.M. errors guanfacine: $8.22\pm1.3$; Tdep= 1.03, df=5, p=0.35). However, the drug produced a highly significant reduction in the number of errors for the never-rewarded (i.e. preferred) object (mean ±S.E.M. errors vehicle: 3.4±0.4; mean ±S.E.M. errors guanfacine: 1.0±0.3; Tdep=8.06, df=5, p=0.0005).). This qualitative anslysis of the 0.1 mg/kg guanfacine response points to an vm/orbPFC mechanism. Guanfacine markedly improved an animal's ability to inhibit reaching for a preferred object when it was not appropriate to task performance, i.e., it decreased impulsivity. Conversely, monkeys with orbital lesions are disproportionately impaired in suppressing a response to a preferred stimulus independent of baiting conditions (Mishkin, 1964). Thus, the pattern of guanfacine-induced improvement is consistent with enhanced orbital function.

Behavioral ratings—all sedation/agitation and aggression scores following saline treatment were 0. Guanfacine's effects on behavioral ratings were analyzed using the Wilcoxon test. Only the 0.5 mg/kg dosage significantly increased sedation ratings (median rating of 2; range 1 to 2; Wilcoxon p=0.043). The 0.1 mg/kg dosage produced a median sedation score of 0; scores ranged from −1 to 1. Thus, the 0.1 mg/kg dose of guanfacine was able to improve reversal performance without inducing significant sedation. The low guanfacine doses had no effect on ratings (all scores 0). Guanfacine's ability to improve reversal performance was clearly dissociated from its sedating effects. The best guanfacine dose (0.1 mg/kg) had no significant effect on behavioral ratings (median score of 0; Wilcoxon n.s.), while the higher dose 0.5 mg/kg) that induced significant sedative effects had a weaker beneficial influence on reversal performance. It is important to note that the aged monkeys used in the current study did not exhibit disinhibited, agitated or aggressive behaviors under baseline (vehicle) conditions, thus limiting the opportunity to observe guanfacine's calming actions. It is likely that guanfacine's calming actions include enhanced behavioral inhibition mediated by the vm/orbPFC, while the sedative actions of alpha-2 agonists appear to involve drug actions in thalamus (Buzsaki et al., 1991), and more global actions mediated through the locus caeruleus (Berridge & Foote, 1991).

Preliminary evidence indicates that these same mechanisms can be observed in a young adult monkey (monkey #320). Guanfacine (0.1 mg/kg) improved object reversal performance from a score of 12/40 trials correct following saline to a score of 31/40 trials correct following guanfacine. This dose of guanfacine had no effect on sedation (sedation scoe of 0). Thus, guanfacine appears to improve ventromedial/orbital prefrontal cortical function in young monkeys as well, and may calm behavior through enhanced ventromedial/orbital prefrontal cortical function.

Example 5
THE EFFECT OF ADMINISTERING GUANFACINE TO CHILDREN AND ADOLESCENTS WITH ATTENTION-DEFICIT/HYPERACTIVITY Based on the calming effects of guanfacine in monkeys, the drug was tested in children and adolescents with Attention-Deficit Hyperactivity Disorder. Parents reported a significant improvement in their children's behavior and functioning during treatment with guanfacine as compared to without guanfacine. This result is supported by the reduction in the overall average score on Conners' Parents Questionnaire (t=2.55, p<0.015). The mean score before medication was 1.27 as compared to the mean score of 0.85 on guanfacine indicating that patients had significantly less Attention-Deficit/Hyperactivity Disorder symptoms during treatment.

Figure 4:
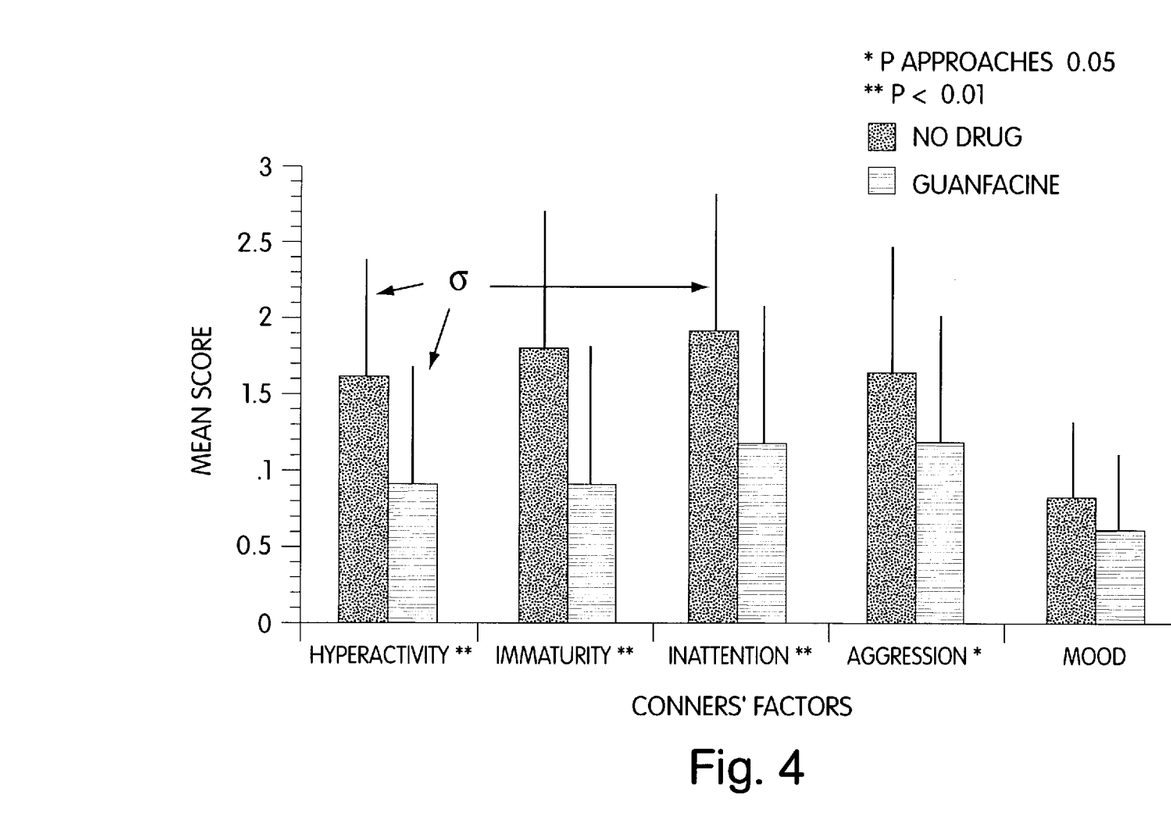
FIG. 4 is a graph depicting the effects of guanfacine in Attention-Deficit Hyperactivity Disorder subjects on Conners rating factors I-V.

Assessment of the Conners' Factors (see FIG. 4) showed a decrease in mean symptoms of hyperactivity (Factor 1: 1.63 off medication, 0.94 on guanfacine; t=3.69, p<0.002), inattention (Factor II: 1.92 off, 1.21 on, t=3.32, p<0.004), and immaturity (Factor V: 1.81 off, 0.92 on, t=3.77, p<0.002). No differences were observed in mood (Factor III) or aggression/opposition (Factor IV), although there was a trend for aggression to be improved. The three patients with symptoms of conduct disorder were rated as more cooperative and less quarrelsome with guanfacine treatment.

Figure 5A:
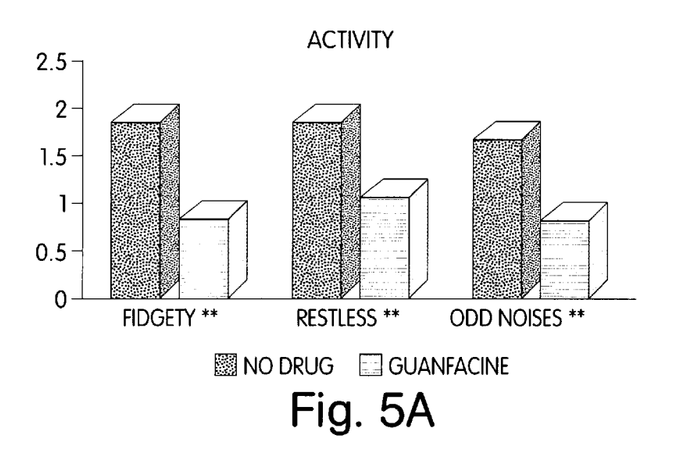
FIGS. 5A–5D are graphs depicting the effects of guanfacine in Attention-Deficit Hyperactivity Disorder subjects on Conners parent ratings of specific items.
Figure 5B:
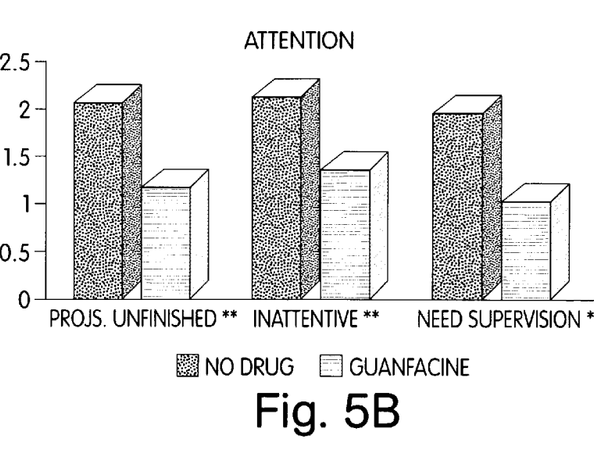
Figure 5C:
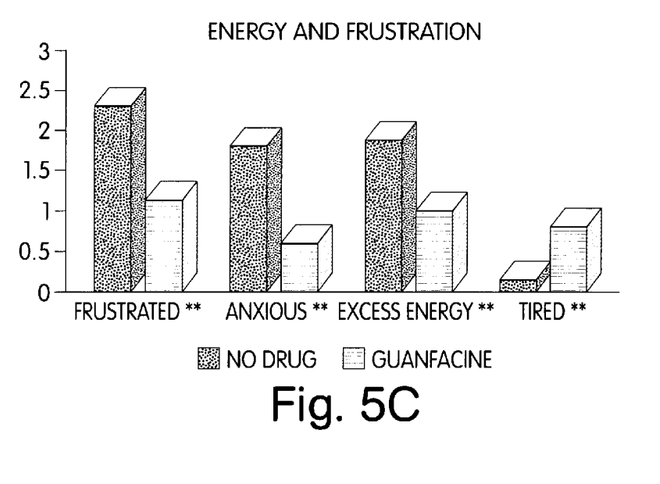

Analysis of the individual items within the Conners' Factors demonstrated specific effects of guanfacine (see FIGS. 5A–C, Table 5). The children were less fidgety (1.85 off, 0.85 on, t=3.61, p<0.002), less restless (1.85 off, 1.08 on, t=2.99, p<0.01) and less likely to make disruptive sounds such as humming and odd noises (1.69 off, 0.85 on, 3.09, p<0.01). In addition, patients were less easily frustrated (2.31 off, 1.17 off, t=3.41, p<0.005), less anxious (1.85 off, 0.69 on, t=3.81, p<0.01) and were more tired during the initial period of treatment (0.14 off, 0.85 on, t=−3.39, p<0.01). However, patients were neither sedated nor impaired in functioning, and did not show significant increases in sleepiness (0.38+/−0.31 off drug, 0.62+/−0.96 on guanfacine(mean +/−S.D.); p>0.4). Interestingly, ten of the subjects (nine male, one female, age range three to eleven years) had previously been treated with clonidine, thus allowing direct comparison between the sedative effects of clonidine and guanfacine. Doses of clonidine (0.2–0.75 mg/day) that produced comparable behavioral calming produced significantly higher sleepiness ratings than found with guanfacine (guanfacine: 0.3+/−1.5; clonidine: 1.0+/−1.1 (mean +/−S.D.), paired t test=2.09, p=0.033 one-tailed). As the sedative effects of alpha-2 agonists became more apparent with increasing age, it is noteworthy that guanfacine was less sedating even though the patients were older than when they were taking clonidine. Patients treated with guanfacine also were better able to finish projects (2.08 off, 1.23 on, t=3.81, p<0.005), more attentive (2.15 off, 1.38 on, t=2.74, p<0.01), and able to function with less supervision (2.00 off, 1.07 on, t=2.35, p<0.025).

Figure 5D:
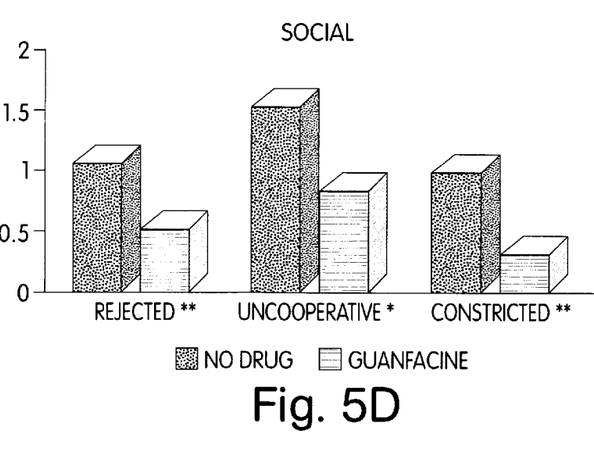

Furthermore, patients improved significantly in some areas of social skills during guanfacine treatment (see FIG. 5D, Table 5). For example, they were less rejected and unpopular in social groups (1.08 off, 0.54 on, t=3.21, p<0.01), less uncooperative (1.54 off, 0.85 on, t=1.81, p<0.05) and less constricted or rigid (1.00 off, 0.33 on, t=2.52, p<0.01).

Subjects did not experience any clinically significant changes in blood pressure nor were any dropped from treatment. A mild transient increase in tiredness usually lasted about 2 weeks. In some cases (16%), a trend toward decreased appetite, which generally stabilized, was noted. Headaches and stomachaches occurred in about 25% of the patients during the first two weeks. These symptoms disappeared in all but one patient who had mild episodes.

The results of this preliminary clinical study indicate that guanfacine is a beneficial and useful treatment for Attention-Deficit/Hyperactivity Disorder. The major beneficial effects of guanfacine are in behaviors reflective of high levels of impulsivity and activity and in cognitive aspects of inhibition and selective attention. Guanfacine appears to facilitate voluntary selective processes essential to willful cognition and discriminant attention. Patients appear to benefit from guanfacine by exhibiting decreased irritability and enhanced affect regulation.

The predominant behavioral effects of calming and improved frustration tolerance, occurring at the expense of only slight sedation, appear most beneficial in highly irritable, hyperactive children. In particular, a wide spectrum of Attention-Deficit/Hyperactivity Disorder patients with associated oppositional-defiant behavior may respond preferentially to guanfacine. Compared to clonidine, guanfacine is less sedating and longer acting. Compared to methylphenidate, guanfacine may be more effective on hyperactivity, low frustration tolerance, and anxiety.

The above data have been published in: Hunt, R. D., Arnsten, A. F. T., Asbell, M. D. (1995). An open trial of guanfacine in the treatment of Attention Deficit Hyperactivity Disorder. J.Amer.Acad.Child Adoles. Psychiatry 34:50–54 (January issue). Based on our non-human primate and clinical research, Horrigan and Barnhill replicated these results in an independent open trial: Horrigan, J. P., Barnhill, L. J. (1995). Guanfacine for treatment of Attention-Deficit Hyperactivity Disorder in boys, J.Child Adolesc. Psychopharm. 5:215–223.

Example 6
THE EFFECT OF ADMINISTERING GUANFACINE TO CHILDREN AND ADOLESCENTS WITH TOURETTE'S SYNDROME For treating children and adolescents having prominent symptoms of Tourette's syndrome, administer guanfacine at doses ranging between 0.01 mg/kg of body weight and 0.25 mg/kg of body weight. Guanfacine was tested in six male subjects, ranging in age from five to fifteen years, who met DSM-IV criteria for Tourette's syndrome. Doses ranged from 2.5–5.0 mg/day. Parent ratings were utilized to assess the level of severity using a four point scale, whereby 0 indicates no tics observed; 1 indicates mild tics observed (approximately one or less per hour); 2 indicates moderate tics observed (approximately one every five minutes); and 3 indicates severe tics observed (approximately one or more per minute). Prior to guanfacine treatment, the mean +/–S.D. tic ratings were 1.83+/–0.56. During guanfacine treatment, tic ratings significantly improved to a mean +/–S.D. of 0.66+/–0.66 (two-tailed T dependent test; no drug vs. guanfacine: p=0.013). Thus, guanfacine may be particularly helpful for children and adolescents with tics who cannot take stimulant medications.

Based on these successful results in monkeys and patients, the Yale Child Study Center (including Dr. Arnsten) initiated an open trial of guanfacine in patients with comorbid Attention-Deficit Hyperactivity Disorder and Tourette's syndrome. Guanfacine significantly improved attention regulation as indicated by improved parent ratings on the Connors scale, and improved performance of a Continuous Performance task. It also produced a mild beneficial effect on tic ratings (Chappell, P. B., Riddle, M. A., Scahill, L., Lynch, K., Schultz, R., Arnsten, A. F. T., Leckman, J. F., Cohen, D. L. (1995), Guanfacine Treatment of Comorbid Attention Deficit Hyperactivity Disorder and Tourette's Syndrome: Preliminary Clinical Experience, J. Am. Acad. Child Adoles. Psychiatry 34:1140–1146)

TABLE 1

THE EFFECTS OF INCREASING DOSE OF GUANFACINE ON BEHAVIOR IN A YOUNG RHESUS MONKEY

| Monkey | Dose (mg/kg) | Average No. Trials (correct/ completed) | Median Agitation/Sedation rating score | Observations |
|---|---|---|---|---|
| #636 | 0 | 10.51/15.3 | –IV | too agitated to complete testing |
| | 0.001 | 11/17 | –IV | too agitated to complete testing |

TABLE 1-continued

THE EFFECTS OF INCREASING DOSE OF GUANFACINE ON BEHAVIOR IN A YOUNG RHESUS MONKEY

| Monkey | Dose (mg/kg) | Average No. Trials (correct/ completed) | Median Agitation/Sedation rating score | Observations |
|---|---|---|---|---|
| | 0.011 | 21/30 | –II | slight agitation |
| | 0.053 | 16/23 | 0 | normal |
| | 0.11 | 22/28 | –II, then I | began a bit agitated, but then sat quietly |
| | 0.53 | 19/30 | –II | slight agitation |

TABLE 2

THE EFFECTS OF 0.53 mg/kg GUANFACINE ON BEHAVIOR IN A YOUNG RHESUS MONKEY: EXAMPLES OF REPLICATIONS

| Monkey | Dose (mg/kg) | Average No. Trials (correct/ completed) | Median Agitation/Sedation rating score | Observations |
|---|---|---|---|---|
| #643 | 0 | 0/0 | –IV | too agitated to test |
| | 0.53 | 23/30 | –II to I | vocal and circling, then calmer |
| | 0 | 16/25 | –IV | too agitated to complete testing |
| | 0.53 | 30/30 | –II | fast, active |
| | 0 | 20/30 | –III | agitation interferred with performance |
| | 0.53 | 27/30 | 0 | normal behavior, attentive |
| | 0 | 0/0 | –IV | too agitated to test |
| | 0.53 | 30/30 | –I | alert and vocal |

TABLE 3

THE EFFECTS OF GUANFACINE ON BEHAVIOR IN AGED RHESUS MONKEYS

| Monkey | Dose (mg/kg) | Average No. Trials (correct/ completed) | Median Agitation/Sedation rating score | Observations |
|---|---|---|---|---|
| #124 | 0 | 18/30 | –II | repeated turning to back of cage, inattentive at times |
| | 0.11 | 19/30 | –II | same as above |
| | 0 | 20/30 | –II | same as above |
| | 0.2 | 26/30 | –I and I | calm but alert, not turning to back of cage |
| #447 | 0 | 18/30 | –II | nervous, easily frustrated, distracted, aggressive when wrong |
| | 0.011 | 18/30 | –II | same, but less aggressive |
| | 0 | 17/30 | –II | nervous, easily frustrated, distracted, aggressive when wrong |

TABLE 3-continued

THE EFFECTS OF GUANFACINE ON BEHAVIOR IN AGED RHESUS MONKEYS

| Monkey | Dose (mg/kg) | Average No. Trials (correct/completed) | Median Agitation/Sedation rating score | Observations |
|---|---|---|---|---|
| | 0.11 | 21/30 | I | calmer and more focused |
| #446 | 0 | 21/30 | 0 | normal, but very aggressive |
| | 0.11 | 20/30 | 0 | same as above |
| | 0 | 22/30 | 0 | same as above |
| | 0.15 | 21/30 | 0 | less aggressive than normal |
| #448 | 0 | 20/30 | 0 | normal, but very aggressive; 3 threat contests in 17 min. |
| | 0.53 | 28/30 | I | calm and much less aggressive; no threat contests |

TABLE 4

THE EFFECTS OF CLONIDINE ON BEHAVIOR IN AGED RHESUS MONKEYS

| Monkey | Dose (mg/kg) | Average No. Trials (correct/completed) | Observations* |
|---|---|---|---|
| #124 | 0 | 20/30 | Aggressive |
| | 0.04 | 27/30 | Very quiet, slow moving. Almost seemed sleepy |
| | 0 | 21/30 | "She was her crazy self" |
| | 0.05 | 23/30 | Very quiet. She did all things slowly . . . seemed sleepy and uncoordinated |
| #447 | 0 | 20/30 | Distracted, lying down and getting up |
| | 0.03 | 20/30 | Sedated a bit-in waves, often inattentive |
| | 0 | 21/30 | Usual self |
| | 0.06 | 28/30 | Falling asleep intermittently |
| #446 | 0 | 21/30 | Aggressive |
| | 0.04 | 23/30 | Sleepy but performing task |
| | 0 | 20/30 | Aggressive |
| | 0.07 | 21/30 | Sleepy but performing task slowly |
| #448 | 0 | 16/30 | Aggressive; throwing plaques |
| | 0.05 | 25/30 | occasional eyes closed, sometimes alert |

*clonidine experiments were conducted in aged monkeys prior to the development of the agitation/sedation rating scale in the other experiments

TABLE 5

SELECTED ITEMS ORDERED BY LEVEL OF SIGNIFICANT CHANGE FROM BASELINE TO GUANFACINE

| | |
|---|---|
| Less Anxious | $P < 0.001$ |
| Less Excess Energy | $P < 0.001$ |
| Better at Finishing Projects | $P < 0.001$ |
| Less Fidgety | $P < 0.002$ |
| Less Easily Frustrated | $P < 0.003$ |
| More Tired | $P < 0.003$ |
| Less Rejected/Unpopular | $P < 0.004$ |
| Less Disruptive Noises | $P < 0.005$ |
| Less Restless | $P < 0.006$ |
| Less Inattentive | $P < 0.009$ |
| Less Constricted/Rigid | $P < 0.010$ |
| Less Need for Supervision | $P < 0.025$ |
| Less Uncooperative | $P < 0.050$ |

Lofexidine

Relatively low doses (0.001–0.01 mg/kg) of lofexidine, were found to calm behavior and improve prefrontal cortical function in young monkeys without evidence of sedative or hypotensive effects.

The examples described below also report an evaluation of the effects of lofexidine on cognitive performance, behavioral ratings and blood pressure in monkeys.

Subjects

The monkeys in the lofexidine study were 8 young female monkeys, with ages estimated to range from about 3–12 years. Of the 8 monkeys, 3 were used for studies of both cognition/behavior and blood pressure, 2 were used for only cognition/behavior experiments, and 3 were used for blood pressure experiments only. The monkeys were housed and cared for at the Yale University School of Medicine, New Haven, Conn.

Cognitive Testing (Monkey studies)

The testing was carried out as described above in connection with guanfacine.

Rating Scales (Monkey Studies)

The testing was carried out as described above in connection with guanfacine.

Blood Pressure

Monkeys were injected with an acute dose of saline vehicle or lofexidine (0.001, 0.01 or 0.05 mg/kg, intramuscularly) 1 hour before blood pressure measurements. Monkeys were lightly anesthetized with ketamine (0.2–0.5 mg/kg with supplementation as needed) 15 min before testing to permit safe handling of the animals. Four blood pressure measurements were taken using a digital, pediatric blood pressure monitor. Both systolic and diastolic blood pressure measurements were recorded. The average of the four measurements was used for each animal.

Drug Administration

Monkeys were injected intramuscularly with an acute dose of lofexidine (0.0001–0.1 mg/kg) one hour prior to cognitive testing/behavioral assessment or blood pressure measurement. There was at least a 10 day washout period between drug treatments. Lofexidine was dissolved in sterile saline under aseptic conditions. For cognitive testing and behavioral assessment, the experimenter testing the animal was unaware of the drug treatment conditions.

Design and Analysis

The testing was carried out as described above in connection with guanfacine.

Figure 6A:
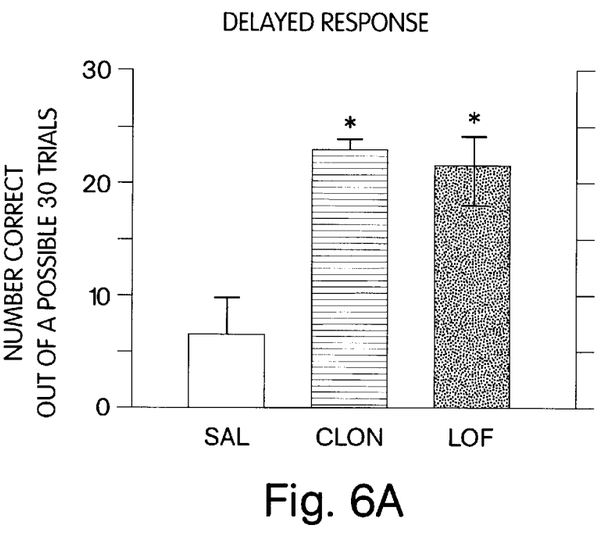
FIGS. 6A and 6B are histograms illustrating the effects of 0.01 mg/kg lofexidine vs. clonidine (0.02–0.05 mg/kg) in young monkeys exhibiting "ADHD-like" symtoms of inattention, agitation, hyperactivity and/or uncooperative behavior.
Figure 6B:
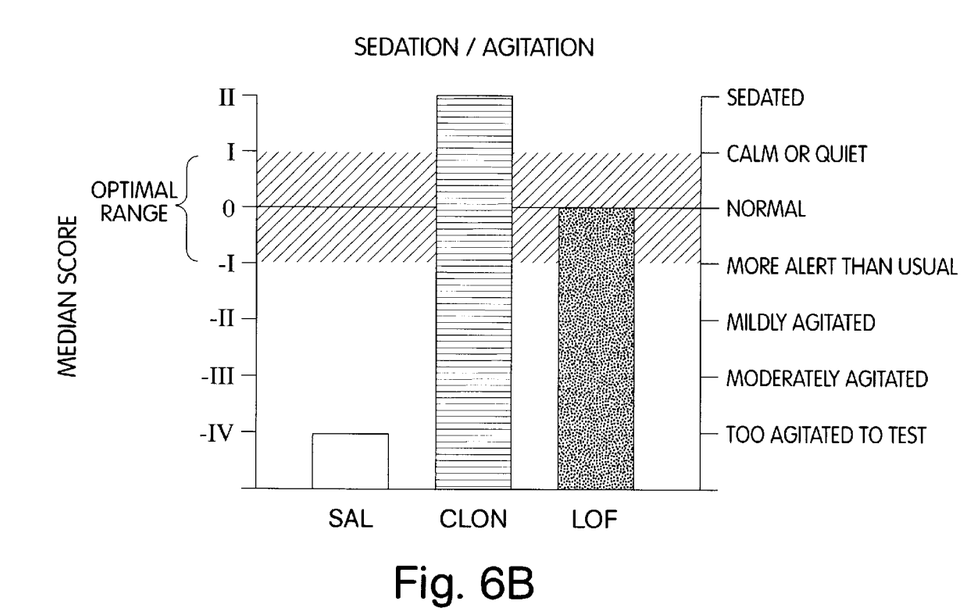

Example 7
THE EFFECT OF ADMINISTERING LOFEXIDINE TO YOUNG, "ADHD-LIKE" MONKEYS Three young monkeys exhibited inattention, uncooperative and/or agitated behavior similar to the symptoms of Attention Deficit Hyperactivity Disorder. When tested on the delayed response task following saline vehicle pretreatment, these monkeys performed poorly (FIG. 6). However, pretreatment with 0.01 mg/kg lofexidine markedly improved performance (FIG. 6). The 0.01 mg/kg lofexidine dose produced no evidence of sedation (median sedation score of 0). These results contrast with those induced by clonidine, where improvement was accompanied by marked sedation (median score of II).

A higher dose of lofexidine (0.05 mg/kg) was tested in one "ADHD-like" monkey. Delayed response performance improved from a score of 7 following vehicle to a score of 26 following lofexidine. However, this higher lofexidine dose did produce sedation (score of II).

Figure 7:
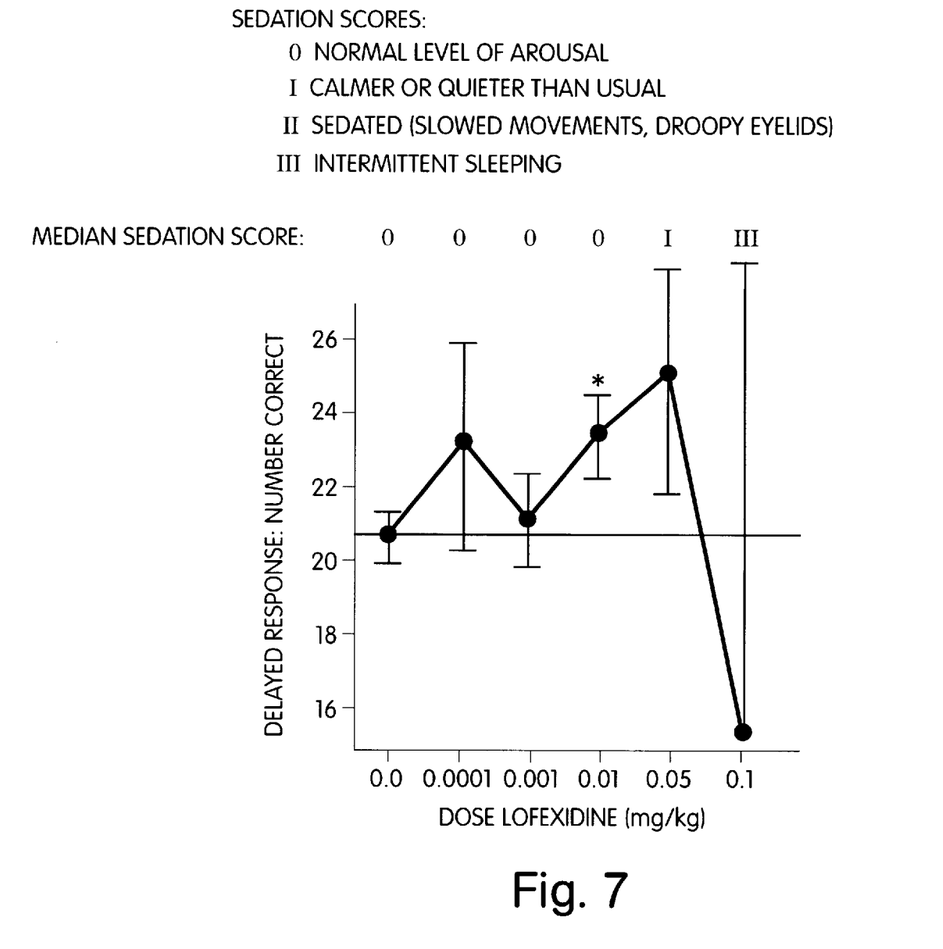
FIG. 7 is a graph illustrating the effects of lofexidine on delayed response performance and median sedation ratings in young monkeys.

Example 8
THE EFFECT OF ADMINISTERING LOFEXIDINE TO NORMAL YOUNG MONKEYS The effects of lofexidine (0.0001–0.1 mg/kg) on delayed response performance and sedation ratings were studied in 5 normal young monkeys (FIG. 7). Lofexidine produced a dose-related improvement in delayed response performance. A few animals were improved in the very low dose range (0.0001–0.001 mg/kg); these doses produced no evidence of sedation (median ratings of 0). There was a significant improvement in delayed response performance following 0.01 mg/kg. This dose produced no sedation (median score of 0). This contrasts with the effects of 0.01 mg/kg clonidine, which produced no improvement in delayed response performance (saline: 20.6±0.9 trials correct; clonidine: 21.4±2.1 trials correct, n=4; not significant), yet produced ratings of "dopey" and "sedated" (II) in half the animals. Thus, unlike clonidine, the 0.01 mg/kg dose of lofexidine was able to improve prefrontal cognitive function without sedation. The 0.05 mg/kg lofexidine dose also improved delayed response performance, and animals were given a median rating score of "I", calmer than usual. At the highest dose tested, sedation emerged (median score of "III", intermittent sleeping; range of scores II–IV). The 0.1 mg/kg dose had variable effects on delayed response performance. While some animals performed near perfectly at this dose, others were interupted by the sedation and performed very poorly. Thus, improvement could be observed over the 0.0001–0.05 mg/kg range without concomitant sedation.

Example 9
THE HYPOTENSIVE EFFECTS OF LOFEXIDINE IN YOUNG MONKEYS

Figure 8A:
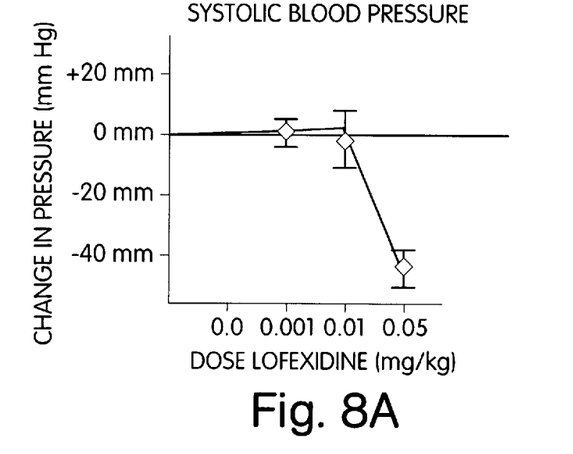
FIGS. 8A and 8B are graphs illustrating the effects of lofexidine on blood pressure (systolic and diastolic) in young monkeys.
Figure 8B:
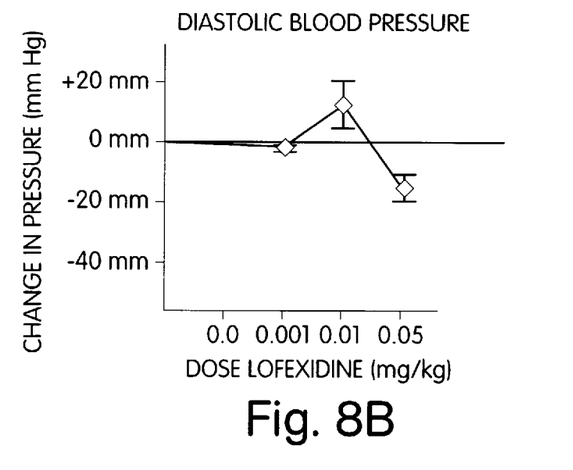

The effects of lofexidine (0.001–0.05 mg/kg) on blood pressure are shown in FIG. 8. Lofexidine doses of 0.001–0.01 mg/kg did not lower systolic or diastolic blood pressure. However, 0.05 mg/kg produced a marked decrease in systolic blood pressure, and a small decrease in diastolic blood pressure. Most importantly, the 0.01 mg/kg dose which significantly improves delayed response performance without sedative side effects similarly showed no effect on blood pressure.

What is claimed is:

1. A method of treating a behavioral disinhibition in a primate without inducing excessive sedation, comprising:
   administering to the primate a behavior inhibiting, non-excessive sedation inducing dose of lofexidine.

2. The method of claim 1, comprising the additional step of readministering the dose at an interval required to obtain a desired level and duration of behavioral inhibition.

3. The method of claim 1, wherein the primate is a human.

4. The method of claim 1, wherein the behavioral disinhibition is one of Attention-Deficit Hyperactivity Disorder, Conduct Disorder, Oppositional-Defiant Disorder, Tourette's Syndrome, Lesch-Nyhan Syndrome, Post-Traumatic Stress Disorder and dementia.

5. A method of inhibiting a disinhibitory behavior in a primate without inducing excessive sedation, said method comprising administering to the primate a behavior inhibiting, non-excessive sedation inducing dose of lofexidine.

6. The method of claim 5, comprising the additional step of readministering the dose at an interval required to obtain a desired level and duration of behavioral inhibition.

7. The method of claim 5, wherein the primate is a human.

8. The method of claim 5, wherein the behavior is one of hyperactivity, agitation, impulsivity, aggression, inattention, distractibility, disorganization, uncontrolled movements, and self-mutilation.

9. The method of claim 1 or claim 5, wherein the dose of lofexidine ranges between 0.001 and 0.05 mg/kg of body weight.

10. A method of treating prefrontal cortical cognitive dysfunction in a schizophrenic patient, said method comprising administering to said patient a cognitive dysfunction-improving, non-excessive sedation inducing amount of lofexidine.

* * * * *